(12) United States Patent
Chinn et al.

(10) Patent No.: US 7,641,687 B2
(45) Date of Patent: Jan. 5, 2010

(54) ATTACHMENT OF A SEWING CUFF TO A HEART VALVE

(75) Inventors: Joseph Andrew Chinn, Shakopee, MN (US); Randall Thoma, San Antonio di saluggia (IT)

(73) Assignee: Carbomedics Inc., Austin, TX (US)

( * ) Notice: Subject to any disclaimer, the term of this patent is extended or adjusted under 35 U.S.C. 154(b) by 295 days.

(21) Appl. No.: 10/979,767

(22) Filed: Nov. 2, 2004

(65) Prior Publication Data

US 2006/0095125 A1    May 4, 2006

(51) Int. Cl.
*A61F 2/24* (2006.01)
(52) U.S. Cl. .................................................. 623/2.4
(58) Field of Classification Search ......... 623/2.1–2.42, 623/900
See application file for complete search history.

(56) References Cited

U.S. PATENT DOCUMENTS

| | | | |
|---|---|---|---|
| 3,574,865 A * | 4/1971 | Hamaker | 623/2.34 |
| 3,655,306 A | 4/1972 | Ross et al. | 425/109 |
| 4,118,806 A | 10/1978 | Porier et al. | 3/1.4 |
| 4,265,694 A | 5/1981 | Boretos et al. | 156/242 |
| 4,364,127 A | 12/1982 | Pierce et al. | 3/1.5 |
| 4,535,483 A * | 8/1985 | Klawitter et al. | 623/2.4 |
| 4,778,461 A | 10/1988 | Pietsch et al. | 623/2 |
| 4,786,556 A | 11/1988 | Hu et al. | 428/412 |
| 4,888,009 A | 12/1989 | Lederman et al. | 623/2 |
| 4,939,007 A | 7/1990 | Hu et al. | 428/34.1 |
| 5,032,666 A | 7/1991 | Hu et al. | 528/70 |
| 5,071,431 A | 12/1991 | Sauter et al. | 623/2 |
| 5,084,315 A | 1/1992 | Karimi et al. | 428/36.6 |
| 5,104,406 A * | 4/1992 | Curcio et al. | 623/2.39 |
| 5,123,919 A | 6/1992 | Sauter et al. | 623/2 |
| 5,139,515 A | 8/1992 | Robicsek | 623/1 |
| 5,397,346 A | 3/1995 | Walker et al. | 623/2 |
| 5,397,348 A | 3/1995 | Campbell et al. | 623/2 |
| 5,545,215 A | 8/1996 | Duran | 623/2 |
| 5,780,807 A | 7/1998 | Saunders | 219/121.71 |
| 5,876,436 A | 3/1999 | Vanney et al. | 623/2 |
| 5,891,195 A | 4/1999 | Klostermeyer et al. | 623/2 |
| 6,143,025 A * | 11/2000 | Stobie et al. | 623/2.39 |
| 6,171,335 B1 | 1/2001 | Wheatley et al. | 623/2.17 |
| 6,299,638 B1 | 10/2001 | Sauter | 623/1.26 |
| 6,352,554 B2 | 3/2002 | De Paulis | 623/1.26 |
| 6,425,916 B1 * | 7/2002 | Garrison et al. | 623/2.11 |
| 6,709,457 B1 * | 3/2004 | Otte et al. | 623/2.4 |
| 6,716,244 B2 | 4/2004 | Klaco | 623/2.4 |
| 6,790,229 B1 * | 9/2004 | Berreklouw | 623/2.1 |
| 6,893,459 B1 * | 5/2005 | Macoviak | 623/2.11 |
| 7,186,265 B2 * | 3/2007 | Sharkawy et al. | 623/2.38 |

(Continued)

OTHER PUBLICATIONS

CarboMedics Inc., "Optiform® Mitral Valve Information for Use" © 2003 CarboMedics Inc.

(Continued)

*Primary Examiner*—Corrine McDermott
*Assistant Examiner*—Cheryl Miller
(74) *Attorney, Agent, or Firm*—Faegre & Benson LLP

(57) ABSTRACT

A heart valve comprises a stent and a sewing cuff comprising a stiffening ring, wherein the stent and the stiffening ring are adapted to be snap-fitted. In one embodiment, the stent and the stiffening ring can together comprise one or more projections and one or more openings.

11 Claims, 4 Drawing Sheets

U.S. PATENT DOCUMENTS

| | | | | |
|---|---|---|---|---|
| 2001/0002445 | A1* | 5/2001 | Vesely | 623/2.11 |
| 2003/0023302 | A1* | 1/2003 | Moe et al. | 623/2.4 |
| 2004/0030381 | A1* | 2/2004 | Shu | 623/2.11 |
| 2004/0186565 | A1* | 9/2004 | Schreck | 623/2.18 |
| 2005/0165479 | A1* | 7/2005 | Drews et al. | 623/2.38 |
| 2005/0240263 | A1* | 10/2005 | Fogarty et al. | 623/2.38 |
| 2006/0271175 | A1* | 11/2006 | Woolfson et al. | 623/2.38 |
| 2007/0255400 | A1* | 11/2007 | Parravicini et al. | 623/2.41 |

OTHER PUBLICATIONS

CarboMedics Inc., "Prosthetic Heart Valve Instructions for Use" © 2003 CarboMedics Inc.

CarboMedics Inc., "Orbis™ Prosthetic Heart Valve Information for Use" © 2003 CarboMedics Inc.

Ward, "Thermoplastic Silicone-Urethane Copolymers: A New Class of Biomedical Elastomers," *Medical Device & Diagnostic Industry* (Apr. 2000).

Ward et al., "High-Strength, Optically Clear, Silicone-UrethaneThermoplastics for Biomedical Use: Bulk Properties," *Sixth World Biomaterials Congress Transactions, Society for Biomaterials*, Minneapolis, MN, p. 431 (2000).

Ward, *Medical Plastics and Biomaterials* 2:34-41 (1995).

Akutsu et al., *J. Appl. Physiol.* 14:1045-1048 (1959).

Bernacca et al., "Hydrodynamic Function of Polyurethane Prosthetic Heart Valves: Influences of Young's Modulus and Leaflet Thickness," *Sixth World Biomaterials Congress Transactions, Society for Biomaterials*, Minneapolis, MN, p. 584 (2000).

Bermacca et al., *The International Journal of Artificial Organs* 20(6):327-331 (1997).

Coleman, *Trans. Am. Soc. Artif. Inter. Organs* 27:708-713 (1981).

Fisher et al., "A New Design of Polymer Synthetic Leaflet Heart Valve," *Sixth World Biomaterials Congress Transactions, Society for Biomaterials*, Minneapolis, MN, p. 68 (2000).

Hanson et al., *J. Lab. Clin. Med.* 95:289-304 (1980).

Hilbert et al., *J Thorac Cardiovasc Surg* 94:419-429 (1987).

Martin et al., *Biomaterials* 21:1021-1029 (2000).

Schoen et al., *J. Biomed. Mater. Res.: Applied Biomaterials* 22(A1):11-36 (1988).

Thoma et al., *Journal of Biomaterials Applications* 3:180-206 (Oct. 1988).

* cited by examiner

REPLACMENT SHEET

ATTACHMENT OF A SEWING CUFF TO A HEART VALVE

BACKGROUND OF THE INVENTION

The present invention relates to the field of heart valves. More particularly, it relates to a valve having a sewing cuff assembly that may be easily and securely coupled to the valve via snap-fitting. In addition, the invention relates to a method for snap-fitting a sewing cuff to a valve.

Prosthetic heart valves are used to replace diseased heart valves in humans. Prosthetic heart valves include mechanical heart valves, bioprosthetic valves, and polymer valves. The term "mechanical valve" as used herein refers to bi-leaflet heart valves comprising a valve orifice fabricated at least in part of a rigid, biologically compatible material such as pyrolytic carbon, and comprising essentially no biological components. The term "bioprosthetic valve" refers to a bi-leaflet or tri-leaflet heart valve comprising at least some biological components such as tissue or tissue components. The biological components of tissue valves are obtained from a donor animal (typically bovine or porcine) or human, and the valve may comprise either biological materials alone or biological materials with man-made supports or stents. The term "polymeric valve" refers to a tri-leaflet, bi-leaflet, or mono-leaflet heart valve comprising at least some elastomeric polymer components, including at least elastomeric polymer valve leaflet(s).

Conventional prosthetic heart valves, whether mechanical, bioprosthetic, or polymer valves, typically include an annular valve body comprising an orifice for blood flow through the valve. The valve body can be made of materials such as biocompatible pyrolitic carbon (mechanical valves), one or more metals or alloys (such as titanium or stellite), porcine or bovine pericardium tissue (bioprosthetic valves), thermoplastics like Delrin or PEEK, or silicone or polyurethane (polymer valves). Leaflets are coupled to the annular body for movement between an open position and a closed position to allow or prevent blood flow through the orifice. Heart valves may include one, two, or three leaflets. The leaflets can be made of pyrolytic carbon, treated tissue, or polymers. The valve is typically attached to a human heart with sutures via a sewing cuff, or some other mechanical attachment means (e.g., staples).

Sewing cuffs generally comprise a toroidal member that is attached to the periphery of the annular valve body to form a site for anchoring sutures to the annulus of the heart during implantation of the heart valve. Sewing cuffs are typically covered with a cloth material, such as polyester, and may also comprise a filler material such as Teflon felt or Dacron cloth. The sewing cuff may be coupled to a peripheral groove on the lower end of the valve body by circumferential cinch-like sutures, or may be mechanically captured adjacent to a stiffening ring.

Existing methods of coupling the sewing cuff to the valve body involve prolonged and repeated handling of the heart valve body. Because attachment of the sewing cuff to the heart valve is a relatively labor-intensive and expensive part of valve fabrication, and because heart valves are more susceptible to damage the more they are handling during assembly, packaging and storage, there is a need for a sewing cuff that can be quickly and securely coupled to the valve body with minimal handling.

There are a number of risks associated with open-heart surgery that are related to the duration of the procedure. Despite advances in blood conservation, the longer it takes to complete a surgical procedure the greater the chance the patient may need a transfusion, which carries with it the risk of transmitting diseases such as HIV or hepatitis, among others. Furthermore, even in the event a procedure is performed successfully, the potential always exists for excessive bleeding over the duration of the procedure, which can result in death of the patient. In addition to problems associated with blood loss and transfusion, a patient connected to a heart-lung machine during a valve replacement procedure may suffer memory loss after surgery. It is therefore desirable to minimize, to the extent possible, the duration of any open heart surgical procedure.

Therefore, there is a need for a heart valve and sewing cuff which can be assembled together with a minimum of handling, and a method for rapidly and securely affixing a sewing cuff to a heart valve. Desirably, the assembled valve would have a low radial thickness of the sewing cuff assembly and a large blood flow orifice area.

SUMMARY OF THE INVENTION

The present invention generally provides a sewing cuff assembly and a heart valve to which the sewing cuff assembly is coupled. The sewing cuff comprises a stiffening ring and the heart valve comprises a stent, wherein the stent and the stiffening ring can be snap-fitted. The invention further provides a method for attaching a sewing cuff assembly to a heart valve by snap-fitting.

In one aspect, embodiments of the invention provide a heart valve comprising a stent and a sewing cuff comprising at least one stiffening ring and a material secured to the stiffening ring. The sewing cuff may include a filler material disposed inside at least a portion of the material secured to the stiffening ring.

BRIEF DESCRIPTION OF THE DRAWINGS

So that the manner in which the above recited features of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DESCRIPTION OF ILLUSTRATIVE EMBODIMENTS

Generally, the present invention relates to a heart valve comprising a stent and a sewing cuff comprising a stiffening ring, wherein the stent and the stiffening ring are adapted to be snap-fitted.

The snap-fitting can be affected by any appropriate means. In one embodiment, the stent comprises one or more projections and the stiffening ring comprises one or more openings, wherein each projection is adapted to be snap-fitted into one of the openings. In another embodiment, the stiffening ring comprises one or more projections and the stent comprises one or more openings, wherein each projection is adapted to be snap-fitted into one of the openings. In an additional embodiment, the stiffening ring comprises at least one opening and at least one projection and the stent comprises at least one projection and at least one opening, wherein each projection of the sewing cuff is adapted to be snap-fitted into an opening of the stent and each projection of the stent is adapted to be snap-fitted into an opening of the sewing cuff.

The word "or" is used herein in the inclusive sense, unless explicitly stated to the contrary.

Figure 1:
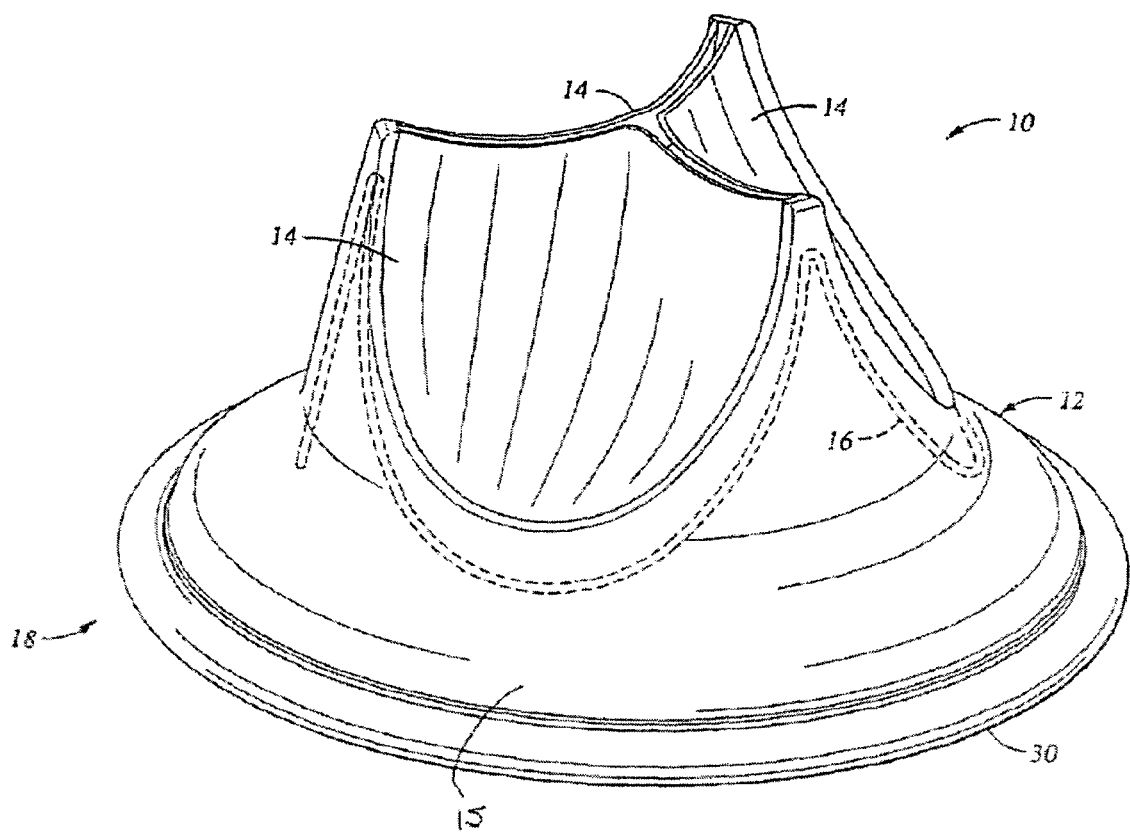
FIG. 1 is a perspective view of an illustrative heart valve having a cuff assembly attached thereto.

FIG. 1 is a perspective view of a prosthetic heart valve 10 having an annular valve body 12 and three flexible leaflets 14. In various embodiments, a prosthetic heart valve can comprise one, two, three, four, or more flexible leaflets. The flexible leaflets can be made of a biocompatible polymer or processed biological tissue, among other materials known in the art. In another embodiment, the heart valve can be a mechanical valve, commonly made from one or more of metal, plastic, graphite, pyrolitic carbon, or other known materials. A mechanical valve can comprise one, two, or more pivoting occluders, a ball-and-cage occluder, or other valve mechanisms known in the art.

Also shown in FIG. 1 is a stent 16, made of metal, plastic, a biocompatible polymer, or any other material, provided the stent is rigid or resiliently deformable. The stent 16 is disposed in or otherwise coupled to the valve body 12 for reinforcement. A sewing cuff, partially shown as reference numeral 30, comprises a stiffening ring 18 and one or more layers of cloth (not shown) connected to the stiffening ring 18. The connection can involve partial or complete gathering of the cloth layer(s) around the stiffening ring 18. The stiffening ring 18 can be made of metal, plastic, or a biocompatible polymer. The cloth layer(s) of the sewing cuff 30 allow(s) a surgeon to suture the prosthetic heart valve 10 to the natural heart.

Further description of exemplary heart valves is given in U.S. Pat. Nos. 5,397,346; 5,397,348; and 6,716,244, the disclosures of which are hereby incorporated by reference.

Illustrative embodiments of the apparatus and technique of the present invention by which the sewing cuff 30 is coupled to the base of the valve body 12 are discussed below and shown in FIGS. 2-6.

Figure 2:
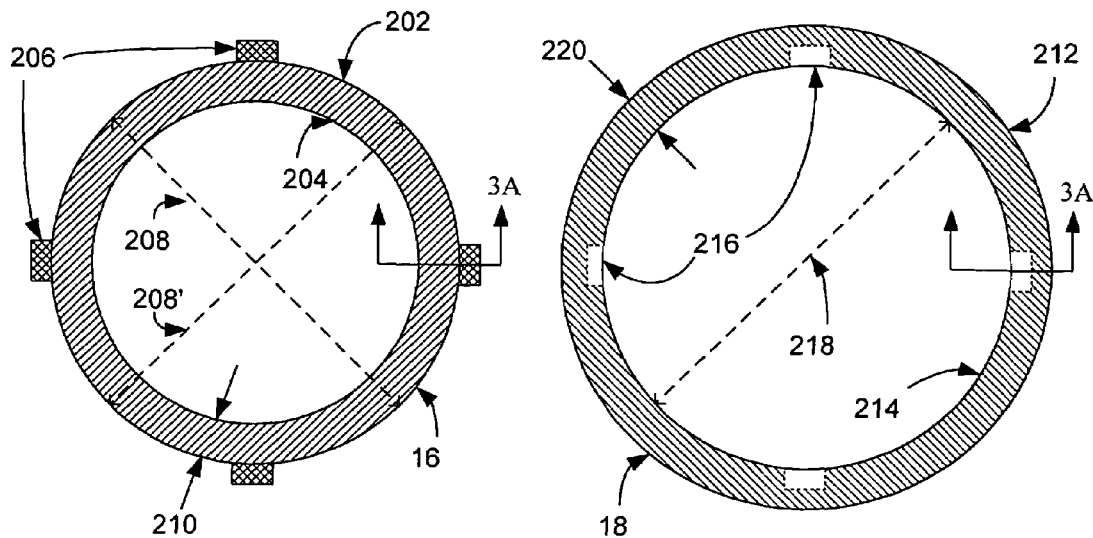
FIG. 2 is a cross sectional view of an illustrative stent and stiffening ring according to one embodiment of the present invention.

FIG. 2 is a cross sectional plan view of a stent 16 and a stiffening ring 18 that may be employed in one illustrative embodiment of the present invention. The stent 16 comprises an outer perimeter 202 and an inner perimeter 204. The stent 16 shown in FIG. 2 is circular, but a stent according to the present invention can have any shape or configuration. The stent 16 has an outer diameter 208 and a radial thickness 210. A first outer diameter 208 and a second outer diameter 208', perpendicular to the first outer diameter 208, define a plane of the stent 16. The stent 16 shown in FIG. 2 also comprises one or more projections 206, wherein each projection 206 projects outward from the stent substantially in the plane. In one embodiment, at least one projection 206 can be formed integrally with the stent 16. In another embodiment, at least one projection 206 is mounted onto the stent 16 after formation of the stent 16 by a screw, adhesive, rivet, or other known attachment means. The outer diameter 208 of the stent 16 can vary as will be apparent to the skilled artisan having the benefit of the present disclosure. In one embodiment, the outer diameter 208 of the stent 16 can be from about 10 mm to about 55 mm.

The particular embodiment of FIG. 2 shows a stent 16 with four projections 206, wherein the projections 206 are disposed in rotational symmetry around the outer perimeter 202. The skilled artisan having the benefit of the present disclosure will recognize that the stent 16 can comprise one, two, three, four, five, six, or an even greater number of projections 206 as a routine matter. The skilled artisan having the benefit of the present disclosure will also recognize that the projections 206 need not be disposed in rotational symmetry around the outer perimeter 202, but that partially symmetrical dispositions and non-symmetrical dispositions can be used as a routine matter. Moreover, the projections 206 may have any desired configuration.

In one embodiment (not shown), the projections 206 can each comprise one or more subprojections.

In one embodiment (not shown), the stent 16 can comprise one projection 206 which is circumferentially disposed around the stent 16.

FIG. 2 shows a stiffening ring 18 comprising an inner perimeter 214 and an outer perimeter 212. The stiffening ring 18 also comprises one or more openings 216. The size and shape of the stiffening ring 18 or any other stiffening ring according to the present invention is not crucial so long as the stiffening ring is adapted in size and shape to mate with a stent of the present invention. Each projection 206 is adapted to be snap-fitted into an opening 216 placed, sized, and shaped to engage the projection 206.

It should be noted that the stiffening ring 18 is a component of sewing cuff 30. The cloth component of the sewing cuff 30 is connected to the stiffening ring 18 at one or more locations. In one embodiment of the sewing cuff 30 (not shown), the cloth is gathered around the stiffening ring 18 such that a layer of cloth lies over at least part of the inner perimeter 214 of the stiffening ring 18, and a hole or holes are introduced in the cloth, before or after gathering around the stiffening ring 18, to reveal each opening 216. In this embodiment, the size and shape of the stiffening ring 18 should account for the thickness of the cloth layer which would be interposed between the stiffening ring 18 and the stent 16. Typical cloth layers have thicknesses from about 10 mils to about 20 mils, though both thinner and thicker cloth layers are contemplated. In this embodiment, the inner diameter 218 of the stiffening ring 18 should be sufficiently greater than the outer diameter 208 of the stent 16 to allow both the cloth layer to be interposed between the stiffening ring 18 and the stent 16 and snap-fitting of the stiffening ring 18 and the stent 16.

In another embodiment of the sewing cuff 30 (not shown), the cloth is connected to the stiffening ring 18 at points other than the inner perimeter 214. For example, the stiffening ring 18 can comprise a groove (not shown) on its outer perimeter 212 which is adapted to engage a lock ring (not shown), wherein the cloth of the sewing cuff is gathered around the lock ring. The lock ring can then be inserted into the groove on the outer perimeter 212 of the stiffening ring 18 to secure the stiffening ring 18 to the rest of the sewing cuff 30.

The stiffening ring 18 has an inner diameter 218 and a radial thickness 220. The inner diameter 218 of the stiffening ring 18 can be the same or slightly greater than the outer diameter 208 of the stent 16. In one embodiment, the inner diameter 218 can be from about 1 mil to about 100 mils greater than the outer diameter 208. In a further embodiment, the inner diameter 218 can be from about 10 mils to about 50 mils greater than the outer diameter 208. In a further embodiment, the inner diameter 218 can be from about 20 mils to about 40 mils greater than the outer diameter 208. The exact relative circumferences are not critical, provided the snap-fit between the stent 16 and the stiffening ring 18 is sufficiently strong for the intended use of the heart valve 10.

The skilled artisan having the benefit of the present disclosure will recognize that the stiffening ring 18 can comprise one, two, three, four, five, six, or an even greater number of openings 216 as a routine matter. The skilled artisan having the benefit of the present disclosure will also recognize that the openings 216 need not be disposed in rotational symmetry around the inner perimeter 214, but that partially symmetrical dispositions and non-symmetrical dispositions can be used as a routine matter. The skilled artisan having the benefit of the present disclosure will further recognize that there will be at least as many openings 216 as there are projections 206, and that the number of openings 216 and the number of projections 206 need not be the same.

The skilled artisan having the benefit of the present disclosure will understand that alternative arrangements of projections and openings are possible as a routine matter. For example, in one embodiment, the stiffening ring 18 can comprise the projections 206, wherein each projection 206 projects from the stiffening ring 18 in the plane of the stent 16, the stent 16 can comprise one or more openings 216, and each projection 206 on the stiffening ring 18 can be snap-fitted into an opening 216 on the stent 16 placed, sized, and shaped to engage the projection 206. For another example, in one embodiment, the stiffening ring 18 has both one or more projections 206 and one or more openings 216, wherein each projection 206 projects from the stiffening ring 18 in the plane of the stent 16, the stent 16 has both one or more projections 206 and one or more openings 216, wherein each projection 206 projects from the stent 16 in the plane of the stent 16; and each projection 206 on the stent 16 or stiffening ring 18 can be snap-fitted into an opening 216 placed on the other of the stent 16 or stiffening ring 18, sized, and shaped to engage the projection 206.

Figure 3A:
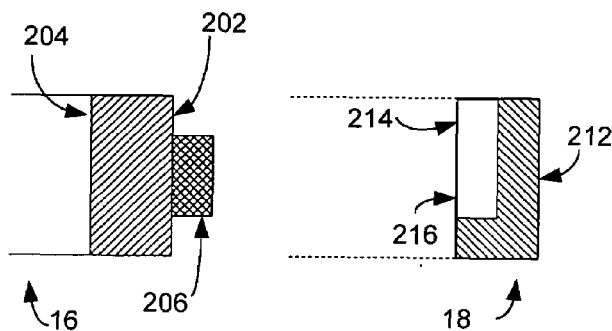
FIG. 3A is a partial cross sectional view of another illustrative embodiment of a stent and a stiffening ring prior to snap-fitting.
Figure 3B:
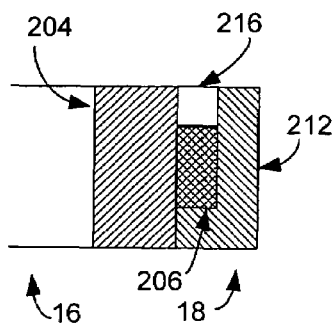
FIG. 3B is a partial cross sectional view of the embodiment of a stent and a stiffening ring of FIG. 3A after snap-fitting.
Figure 4A:
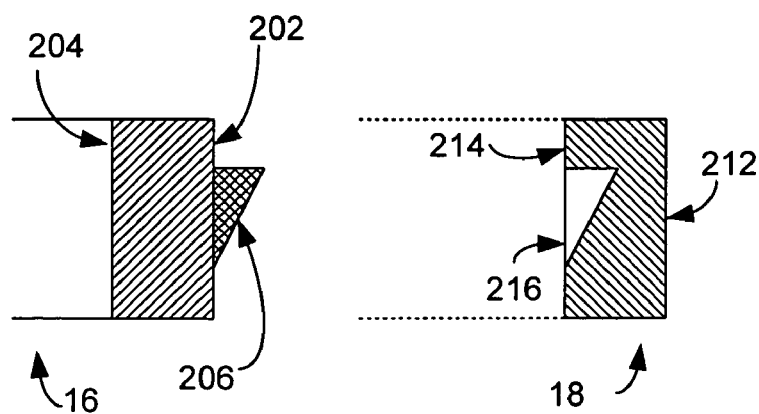
FIG. 4A is a partial cross sectional view of another illustrative embodiment of a stent and a stiffening ring prior to snap-fitting.
Figure 4B:
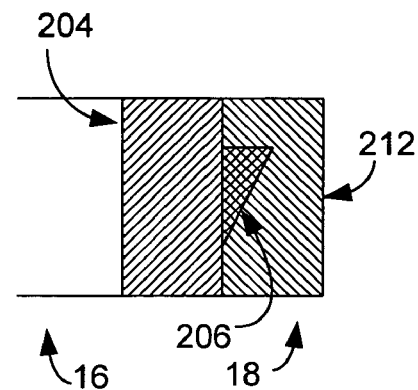
FIG. 4B is a partial cross sectional view of the embodiment of a stent and a stiffening ring of FIG. 4A after snap-fitting.

FIGS. 3 and 4 are partial, cross sectional side views of a projection area of the stent and an opening area of the stiffening ring along the lines 3A in FIG. 2. In FIG. 3A, the illustrative projection 206 is rectangular in cross section, and the opening 216 is also rectangular in cross section. The embodiment of FIG. 3A can be used when the stent 16 is rigid. In FIG. 4A, the projection 206 is wedge-shaped in cross section, and the opening 216 is also wedge-shaped in cross section. The embodiment of FIG. 4A can be used when the stent 16 is resiliently deformable. Upon snap-fitting, the projection 206 is seated in the opening 216, as shown in FIGS. 3B and 4B. The skilled artisan having the benefit of the present disclosure will understand other embodiments of the projections 206 and the openings 216 are possible and within the scope of the present invention.

The particular geometry of the projection 206 and the opening 216 is not critical, provided each opening 216 is placed, sized, and shaped to engage a projection 206 by snap-fitting, taking into account whether the material of the stent 16 or the stiffening ring 18 is rigid or resiliently deformable. The projection 206 can be rectangular, wedge-shaped, or have some other shape. Multiple projections 206 can have the same shape or different shapes. Multiple projections 206 can have the same size or different sizes. Multiple projections 206 having different sizes, shapes, or both can be useful to impart an asymmetry to the stent 16, the stiffening ring 18, or the heart valve 10 in order to guide the surgeon to implant the heart valve 10 in a particular orientation, among other possibilities.

Figure 5:
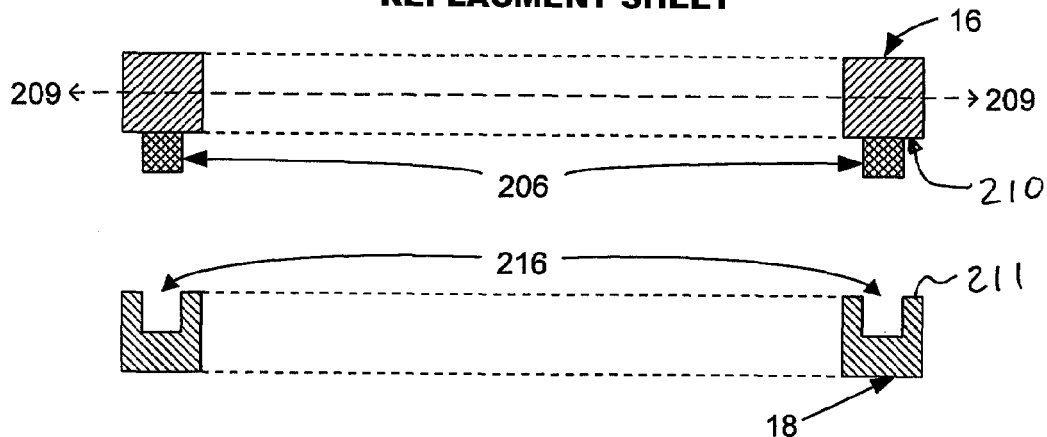
FIG. 5 is a side view of an illustrative stent and stiffening ring according to one embodiment of the present invention.

FIG. 5 shows a side view of a stent and a stiffening ring according to another embodiment of the invention. In this embodiment, the stent 16 has a plane 209, a generally planar mating surface 210, and one or more projections 206 projecting outward from the mating surface 210 of the stent 16 perpendicular to the plane 209. The projections 206 and the openings 216 can be as defined above. The stiffening ring 18 comprises a generally planar mating surface 211 and one or more openings 216 in the mating surface 211 to engage the projections 206.

Figure 6A:
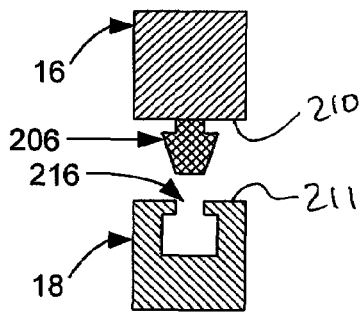
FIG. 6A is a partial cross sectional view of an embodiment of a stent and a stiffening ring prior to snap-fitting.
Figure 6B:
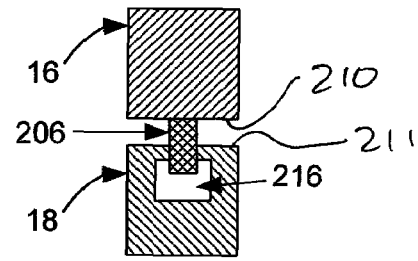
FIG. 6B is a partial cross sectional view of an embodiment of a stent and a stiffening ring during insertion of a projection of the stent into an opening of the stiffening ring.
Figure 6C:
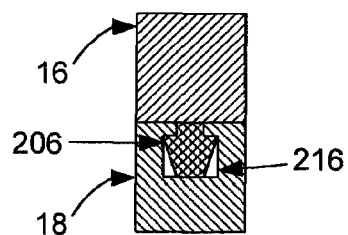
FIG. 6C is a partial cross sectional view of an embodiment of a stent and a stiffening ring after snap-fitting.

In one embodiment, shown in FIGS. 6A-6C, the projections 206 are resiliently deformable and the projections 206 and the openings 216 are adapted to lock the projections 206 into the openings 216 upon engagement. The skilled artisan having the benefit of the present disclosure will understand other embodiments of the projections 206 and the openings 216 are possible and within the scope of the present invention.

The skilled artisan having the benefit of the present disclosure will understand that the alternative arrangement of projections and openings is possible as a routine matter, i.e., that in one embodiment, the stiffening ring comprises one or more projections substantially perpendicular to the plane of the stent, the stent has one or more openings, and each projection can be snap-fitted into an opening placed, sized, and shaped to engage the projection. In another embodiment, the stiffening ring has both one or more projections substantially perpendicular to the plane of the stent and one or more openings, the stent has both one or more projections substantially perpendicular to the plane of the stent and one or more openings, and each projection can be snap-fitted into an opening placed, sized, and shaped to engage it.

In another embodiment, the present invention relates to a method of attaching a sewing cuff to a heart valve, comprising:

snap-fitting a stent and a sewing cuff comprising a stiffening ring, wherein the stent and the stiffening ring are adapted to be snap-fitted.

Any stent and stiffening ring described above can be used in the present method. The stent and the stiffening ring can comprise any means for snap-fitting. In one embodiment, the stent and the stiffening ring can each comprise projections, openings, or both, such that an opening can engage each projection.

If the stent is rigid, the projections and openings can be formed such that snap-fitting can comprise pushing the stent onto the stiffening ring. A stent made of metal may be rigid. If the stent is resiliently deformable, at least some of the projections and openings can be formed such that snap-fitting can comprise applying a deforming force to the stent, inserting the stent into the stiffening ring such that, when the deforming force is removed, the projections and openings can mate, and then removing the deforming force. A stent made of plastic may be resiliently deformable. If the stent comprises resiliently deformable projections, snap-fitting can comprise inserting a projection into an opening such that the projection is resiliently deformed by the stiffening ring until the projection locks into mate with the opening.

While the foregoing description is directed to particular embodiments of the present invention, other and further embodiments of the invention may be devised without departing from the basic scope thereof, and the scope thereof is determined by the claims that follow.

What is claimed is:

1. A heart valve, comprising:
   an annular stent having first and second outer diameters defining a horizontal plane, the stent including a generally planar first mating surface and a plurality of resiliently deformable projections extending from first mating surface of the stent in a direction generally perpendicular to the horizontal plane of the stent; and
   an annular sewing cuff comprising a stiffening ring including a generally planar second mating surface and a plurality of openings in the second mating surface each configured to receive one of the projections,
   wherein the stent and the stiffening ring are adapted to be snap-fitted together with the first and second mating surfaces contacting one another and each projection snap-fitted into one of the openings.

2. The heart valve of claim 1, wherein the stent comprises three projections and the stiffening ring comprises three openings.

3. The heart valve of claim 1, wherein the stent comprises four projections and the stiffening ring comprises four openings.

4. The heart valve of claim 1, wherein the stent is made from polymer or metal.

5. The heart valve of claim 1, wherein the stiffening ring is made from polymer or metal.

6. A method of attaching a sewing cuff to a heart valve, comprising:
   snap-fitting a stent and a sewing cuff, the stent having first and second outer diameters defining a horizontal plane and including a generally planar first mating surface and a plurality of resiliently deformable projections extending from first mating surface in a direction generally perpendicular to the horizontal plane of the stent, the sewing cuff comprising a stiffening ring including a generally planar second mating surface and a plurality of openings in the second mating surface each configured to receive one of the projections of the stent, including snap-fitting the stent and the stiffening ring together with the generally planar first and second mating surfaces of the stent and stiffening ring, respectively, in contact with one another and each of the projections snap-fitted into one of the openings.

7. The method of claim 6, wherein the stent comprises three projections and the stiffening ring comprises three openings.

8. The method of claim 6, wherein the stent comprises four projections and the stiffening ring comprises four openings.

9. The method of claim 6, wherein the stent is made from polymer or metal.

10. The method of claim 6, wherein the stiffening ring is made from polymer or metal.

11. A heart valve, comprising:
    an annular stent having first and second outer diameters defining a horizontal plane, the stent including a generally planar mating surface and a plurality of openings in the generally planar mating surface of the stent;
    an annular sewing cuff including a stiffening ring, the stiffening ring including a generally planar mating surface and a plurality of resiliently deformable projections extending from the generally planar mating surface of the stiffening ring in a direction generally perpendicular to the horizontal plane of the stent, each of the projections adapted to be snap-fitted into one of the openings of the stent,
    wherein each of the projections of the stiffening ring is snap-fitted into one of the openings in the stent to couple the stent to the sewing cuff with the generally planar mating surfaces of the stent and stiffening ring in contact with one another.

* * * * *

UNITED STATES PATENT AND TRADEMARK OFFICE
CERTIFICATE OF CORRECTION

PATENT NO. : 7,641,687 B2
APPLICATION NO. : 10/979767
DATED : January 5, 2010
INVENTOR(S) : Chinn et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 590 days.

Signed and Sealed this

Sixteenth Day of November, 2010

David J. Kappos
*Director of the United States Patent and Trademark Office*